United States Patent [19]

Nafziger et al.

[11] Patent Number: 5,130,551
[45] Date of Patent: Jul. 14, 1992

[54] NAIL DRYING APPARATUS

[75] Inventors: Michael D. Nafziger; Roger L. Davis, both of Mesa, Ariz.

[73] Assignee: Ultraset Limited Partnership, Scottsdale, Ariz.

[21] Appl. No.: 394,200

[22] Filed: Aug. 15, 1989

Related U.S. Application Data

[63] Continuation-in-part of Ser. No. 235,349, Aug. 23, 1988, abandoned.

[51] Int. Cl.⁵ .............................................. G21K 5/00
[52] U.S. Cl. ........................ 250/492.1; 250/504 H; 34/202; 118/642
[58] Field of Search ............... 118/504, 642; 34/202; 250/492.1, 493.1, 504 H, 515.1

[56] References Cited

U.S. PATENT DOCUMENTS

| | | | |
|---|---|---|---|
| 2,085,627 | 6/1937 | Bodman | 250/504 H |
| 2,374,472 | 4/1945 | Corbett | 34/202 |
| 2,490,019 | 12/1949 | Elliot | 34/202 |
| 2,673,402 | 3/1954 | Chambers | 34/202 |
| 3,287,824 | 11/1966 | Selditz | 34/202 |
| 4,731,541 | 3/1988 | Shoemaker | 250/492.1 |

Primary Examiner—W. Gary Jones
Assistant Examiner—Charles K. Friedman
Attorney, Agent, or Firm—Harry M. Weiss

[57] ABSTRACT

A nail drying apparatus by which any commercially available nail polish of any color can be dried after being applied to a person's finger or toe nails. The apparatus consists of a photo-reactive coating and a device that generates ultraviolet radiation. The photo-reactive coating is applied over the wet nail polish and then irradiated with safe dosages of ultraviolet radiation causing the nail polish to dry in a few minutes.

28 Claims, 1 Drawing Sheet

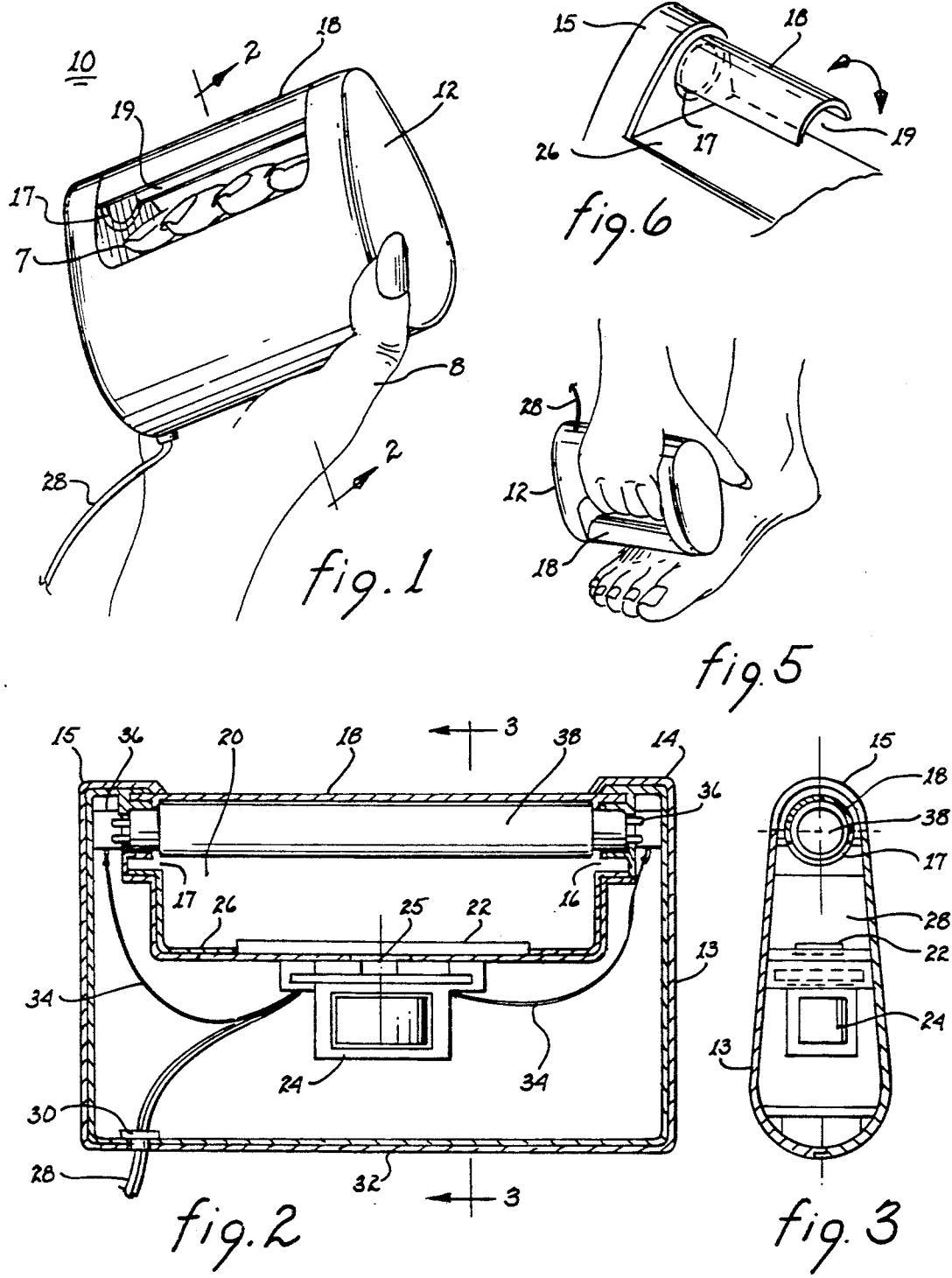

NAIL DRYING APPARATUS

RELATED APPLICATION

This application is a continuation-in-part of our earlier application, Ser. No. 235,349 filed Aug. 23, 1988 now abandoned.

BACKGROUND OF THE INVENTION

1. Field of Invention

This invention generally relates to an apparatus and method therefor for rapidly drying a nail polish or enamel that has been applied to a human nail; more particularly, the invention concerns an apparatus and method therefor that first applies a coating of a photo-reactive chemical to a freshly polished nail and then exposes the nail to ultraviolet radiation which reacts with the coating and completely dries the nail polish within three minutes.

2. Background of the Invention

In the past, nail polish and enamels were air dried after they were applied. This process required a very long period of time before the nail polish dried on the nails. While waiting for the polish to dry, the polish wearer had to avoid touching the surface of the nails, or else the polish would smear or smudge, resulting in a ruined manicure. In effect, the wearer was prevented from using their hands in any normal everyday activity while the polish was drying. This especially proved burdensome for salon customers who needed to manipulate purses, car keys and other objects immediately after receiving a manicure.

Realizing the burden that air drying method put on people with freshly manicured hands, devices were developed to try to expedite the drying process. (See, U.S. Pat. Nos. 2,374,472 and 2,262,274) These devices generally consisted of a box-like dryer which blew or circulated hot or cold air onto the nail's surface for a specified period of time. However, these devices could only dry the top coating on the nail and did not dry the nail polish underneath the top coating. Consequently, additional exposure to the air was required to dry the lower coatings of nail polish and the manicure was still easily ruined if the nail's surface came into contact with another hard surface. As a result, nail polish wearers still had to use their hands cautiously for several hours so as not to ruin the manicure.

U.S. Pat. No. 3,928,113 discloses a process for coating nails comprised of the steps of applying a water soluble base coat to the nails, allowing the base coat to dry, then applying a photocurable nail lacquer and curing the lacquer by exposing it to sufficient amounts of radiation. The alleged inventive purpose behind this patent was to try to develop a nail coating that could be removed by water instead of by an acetone based commercially available nail polish remover. Accordingly, the nail lacquer was specifically designed for a water soluble base coat and commercially available nail polishes could not be used in the process. U.S. Pat. No. 4,596,260 discloses a process of applying a photocurable coating to an artificial nail tip whereby upon exposure to suitable radiation the coating hardens to give the appearance of a natural nail. The photocurable coating being devoid of any solvents is very difficult to remove if applied to commonly used nail polishes. Thus, while both these reference are relevant to show the general state of the art, neither is directed to the inventive purpose behind the subject invention which is to rapidly dry any commercial available nail polish and enamel.

Accordingly, a need still exists for a nail drying apparatus and method therefore, which utilizes ultraviolet radiation, in safe dosages, and a photo-reactive coating, that can dry any commercially available nail polishes and enamels after they have been applied to a human nail.

SUMMARY OF THE INVENTION

An object of the present invention is to provide a nail drying apparatus and method therefor which utilizes both ultraviolet radiation, in safe dosages, and a photo-reactive nail coating.

Another object of the present invention is to provide a nail drying apparatus and method therefor which rapidly dries nail polish and enamel.

Yet another object of the present invention is to provide a nail drying apparatus and method therefor that provides rapid drying of nail polish that can be removed by ordinary and commercially available nail polish remover.

Yet another object of the present invention is to provide a nail drying apparatus and method therefor that can be used to dry any commercially available nail polish of any color.

Presently, in nail salons and homes around the world, nail polish is applied in a three step process.

First, a base-coat is used to fill ridges in the nail and to prevent the colored polish or enamel, applied in step two, from staining the natural nail.

Second, two coats of colored polish or enamel are applied. Two coats are usually used in order to provide an opaque and colorful finish.

Third, a clear top coat is applied to protect the nail polish or enamel, applied in step two, to give it a prominent shine and provide extended wear.

The present invention provides a coating for nails that is applied to the nails as the top coat in step three. Like, present day top coats this coating is clear, imparts a prominent shine, and also provides extended wear. Unlike present day top coats, the coating is photo-reactive. Thus, after this coating has been applied as a top coat the present invention also provides a source of ultraviolet radiation, in safe dosages, that irradiates the top coat causing the coating to react which results in the nail polish or enamel underneath drying within a few minutes.

These and other objects, features and advantages of the present invention, as well as details of the preferred embodiment thereof, will be more fully understood from the following description and drawing.

BRIEF DESCRIPTION OF THE DRAWING

FIG. 1 is a perspective view of the preferred embodiment of the component of the present invention that emits ultraviolet radiation;

FIG. 2 is a cross-sectional view of the preferred embodiment of FIG. 1 along line 2—2 of FIG. 1;

FIG. 3 is a cross-sectional view of the preferred embodiment of FIG. 1 along line 3—3 of FIG. 2;

FIG. 4 is an electrical schematic;

FIG. 5 is a view of the preferred embodiment of FIG. 1 being used on toe nails; and FIG. 6 shows the eyeshield connected to the housing.

DESCRIPTION OF THE PREFERRED EMBODIMENT

The photo-reactive coating is comprised of solvents, primary film former, photocurable monomers, an oligomer, a photoinitiator and an inhibitor. As these ingredients are commonly found in nail coating products, one skilled in the art would readily understand the purpose for each of these in the photo-reactive coating. Consequently, these ingredients need not be discussed in great detail. In the preferred embodiment of the coating, the solvents are Ethyl Acetate and Butyl Acetate, the primary film former is Nitrocellulose. The use of these solvents and primary film former allow the coating to be removed by any commercially available acetone based nail polish remover and improves the coating's compatibility with commercially available colored nail enamels and polish. The coating is formulated to react with long wavelength ultraviolet radiation as this radiation will not harm human skin or eyes if exposed for short periods of time. In the preferred embodiment, the coating is comprised by weight, within + or −10%, of:

Ethyl Acetate . . . 30%
Butyl Acetate . . . 5%
Nitrocellulose . . . 35%
Ethyl Methacrylate . . . 20%
Oligomer . . . 5%
Photoinitiator . . . 5%
Inhibitor . . . >1%

An example of a photoinitiator that could be used in the preferred embodiment is Darocure 1173 distributed by EMI Industries of New York City. Likewise, Butane Dio Dicylate could be used as the Oligomer and Methylethyl Hydroquinone as the inhibitor.

As would be appreciated by one skilled in the art, these chemicals were selected, in part, because they are non-toxic and generally non-photoallergenic.

Referring to the drawings, FIGS. 1-3 show the ultraviolet radiation emitting device generally designated by reference number 10 comprised of a housing 12 having an ovate shape to enable the device to fit easily and snugly into the palm of a user's hand 8. The housing 12 is preferably formed from a lightweight plastic and has a base section 13 and two parallel integral arm members 14 and 15 that extend out from the base section 13. Each arm member 14 and 15 has a circular groove 16 and 17 respectively. The grooves 16 and 17 have the same dimensions and are positioned to face and be aligned with each other. An eyeshield 18 is rotatably connected to the arm members 14 and 15 by sliding each end of the eyeshield 18 into the grooves 16 and 17 (see FIG. 6). Enclosed by arm members 14 and 15, eyeshield 18 and the top side 26 of the base section 13 is a gripping means 20 through which the user can place his/her fingers 7 when grasping the device 10. Extending along the top side 26 is an on/off switch 22. The switch 22 is electrically coupled to an electric ballast 24 through a hole 25 on the top side 26. A power cord 28 runs from the electric ballast 24, through a hole in the bottom side 32 of base section 13, to an external power source. Electric wires 34 are connected at one end to the electric ballast 24 and run up through arm members 14 and 15 and connect at their other end to electric sockets 36. Between the electric sockets 36 is coupled a fluorescent light bulb 38 that emits long wave ultraviolet radiation and is of the type generally commercially available such as a F4T5/350 blacklight bulb for example, (FIG. 4 shows the electrical circuit for this device).

It should be known to one trained in the art that ultraviolet radiation in the medium to short wavelengths (UV-B and UV-C) can be harmful to human skin and eyes. Thus in the preferred embodiment the light bulb 38 would emit ultraviolet radiation in the long wavelengths (UV-A) from about 320 to 390 nanometers. While it is recognized that exposure even to long wavelength ultraviolet radiation may be harmful to a person's skin and eyes if such exposure is for long periods of time in the preferred embodiment of the present invention exposure times of only about three minutes will be required. Also, it is preferable that the light bulb 38 be fluorescent instead of incandescent because fluorescent light bulbs emit 80 percent light and 20 percent heat while incandescent light bulbs emit 80 percent heat and 20 percent light.

In the preferred embodiment, the eyeshield 18 is curved creating a parabolic channel 19 which encompasses the light bulb 38. The eyeshield 18 is made of a material that is opaque to ultraviolet radiation and is normally positioned to direct ultraviolet radiation onto the switch 22 and the top side 26.

The operation of the present invention is simple and easy. First, the power cord 28 is connected to an external power source and if needed the eyeshield 18 is rotated to the normal position. Then the user follows steps one and two of the common procedure (described on page 4 of this application) for applying any commercially available nail polish to his/her nails. In step three of the common procedure, the photo-reactive coating is applied. The user then grasps gripping means 20. By grasping gripping means 20, the user's fingernails are automatically positioned to be irradiated by the light bulb 38 and the user's fingertips are automatically positioned on top of switch 22. The user then presses down and then releases the switch 22, thereby energizing the light bulb 38. Once the light bulb 38 is energized, the fingernails are irradiated with long wave ultraviolet radiation and the photoreactive coating chemically binds and reacts with the fresh nail polish underneath drying the nail polish in about three minutes. The device 10 is turned off by again pressing down and releasing the switch 22. The user can then switch hands and repeat the process or alternatively the user can rotate the eyeshield 18 and irradiate the nails on the other hand or on a foot (see FIG. 5).

While the invention has been particularly shown and described with reference to a preferred embodiment thereof, it will be understood by those skilled in the art that changes in form and detail may be made therein without departing from the spirit and the scope of the invention.

I claim:

1. A nail polish drying apparatus comprising:
   a housing member of ovate cross section having a bottom portion and a top portion, said bottom portion being larger in width than said top portion, said apparatus having a length of sufficient size to permit a user to grip the bottom portion of said housing member in one hand;
   a horizontally extending opening located in the top portion of said apparatus having a width and length of sufficient size to permit the user to insert at least four fingers of one hand into said opening while holding the bottom portion of said housing member in one hand;
   means located within said opening for emitting ultraviolet radiation to simultaneously shine on at least four of the fingernails of the user's hand such that a photo-reactive coating applied over a nail polish is cured by sufficient exposure to said ultraviolet radiation.

2. The apparatus of claim 1 wherein said coating is applied as a top coat over said nail polish.

3. The apparatus of claim 1 wherein said coating is a transparent coating.

4. The apparatus of claim 1 wherein said coating chemically binds with and rapidly dries any commercially available nail polish of any color upon said exposure.

5. The apparatus of claim 1 wherein said coating is removable by any commercially available nail polish remover.

6. The apparatus of claim 1 wherein said coating is water resistant.

7. The apparatus of claim 1 wherein said coating is resistant to mild organic acids.

8. The apparatus of claim 1 wherein said coating is homogeneous.

9. The apparatus of claim 1 wherein said coating is comprised of sufficient amounts of solvents, primary film former, photocurable monomer, photocurable oligomer, photoinitiator and inhibitor.

10. The apparatus of claim 9 wherein said coating includes from about 30% to about 70%, by weight, of said solvents and from about 20% to about 35% by weight of said primary film former.

11. The apparatus of claim 10 wherein said solvents are Ethyl Acetate and Butyl Acetate and said primary film former is Nitrocellulose.

12. The apparatus of claim 9 wherein said coating is by weight as follows:

Ethyl Acetate ... in the range from about 20% to about 40%

Butyl Acetate ... in the range from about 1% to about 15%

Nitrocellulose ... in the range from about 25% to about 45%

Ethyl Methacrylate ... in the range from about 10% to about 30%

Oligomer ... in the range from about 1% to about 15%

Photoinitiator ... in the range from about 1% to about 15%

Inhibitor ... >1%

13. The apparatus of claim 1 wherein said ultraviolet radiation has a wavelength from about 320 nanometers to about 390 nanometers.

14. The apparatus of claim 1 wherein said means for emitting is further comprised of:
means for generating said ultraviolet radiation; and
means within said top portion for enclosing and supporting said means for generating.

15. The apparatus of claim 14 wherein said means for generating is operably connected to an energy source.

16. The apparatus of claim 15 wherein said energy source is conventional household alternating electrical current.

17. The apparatus of claim 15 wherein said energy source is D.C. electrical current produced by conventional batteries.

18. The apparatus of claim 14 wherein said housing member is light-weight and portable.

19. The apparatus of claim 14 wherein said housing member is shaped to fit into the palm of the user's hand.

20. The apparatus of claim 14 further comprising switch means for turning on and off said means for generating.

21. The apparatus of claim 14 wherein said means for generating is a fluorescent light bulb.

22. The apparatus of claim 21 wherein said light bulb is a long wavelength ultraviolet black light bulb.

23. The apparatus of claim 21 wherein said housing member includes;
eyeshield means for directing said ultraviolet radiation in substantially one direction; and said opening having;
gripping means for allowing said housing member to be grasped by the user's left or right hand.

24. The apparatus of claim 23 wherein said eyeshield means is rotatably coupled to said housing member over the entire range of 360 degrees.

25. The apparatus of claim 23 wherein said eyeshield means is normally positioned to direct said ultraviolet radiation onto said gripping means.

26. The apparatus of claim 23 wherein said gripping means causes the user's fingernails to align in a row across said gripping means when said housing member is grasped by the user.

27. The apparatus of claim 26 wherein said gripping means is positioned a sufficient distance from said means for generating to permit the rapid drying of said nail polish after said coating has been applied.

28. The apparatus of claim 27 wherein said switch means is positioned below said gripping means so that said generating means can be turned on and off by pressing and depressing said gripping means.

* * * * *